United States Patent
Yoshizawa et al.

[11] Patent Number: 5,432,760
[45] Date of Patent: Jul. 11, 1995

[54] METHOD OF MEASURING PHASE DIFFERENCE OF OPTO-MAGNETIC RECORD MEDIUM AND APPARATUS FOR CARRYING OUT SAID METHOD

[75] Inventors: Akihiko Yoshizawa; Yasuhiro Fujiwara, both of Hachioji, Japan

[73] Assignee: Olympus Optical Co., Ltd., Japan

[21] Appl. No.: 55,906

[22] Filed: May 3, 1993

Related U.S. Application Data

[63] Continuation of Ser. No. 514,683, Apr. 19, 1990, abandoned.

[30] Foreign Application Priority Data

Apr. 19, 1989 [JP] Japan ................... 1-99200
Nov. 21, 1989 [JP] Japan ................... 1-300661

[51] Int. Cl.$^6$ ........................................ G11B 11/00
[52] U.S. Cl. ........................................ 369/13; 369/110
[58] Field of Search .............. 369/110, 54, 117, 124, 369/106, 107, 13, 44.32, 122, 58, 271; 360/59, 114; 359/11, 279; 356/358, 350; 250/205, 201.5

[56] References Cited

U.S. PATENT DOCUMENTS

| | | | |
|---|---|---|---|
| 3,614,195 | 10/1971 | Vollmer | 359/371 |
| 3,748,597 | 7/1973 | Reinhart | 359/279 |
| 3,780,296 | 12/1973 | Waksberg et al. | 250/201.5 |
| 4,071,751 | 1/1978 | Waksberg | 250/205 |
| 4,342,517 | 8/1982 | Johnson et al. | 356/350 |
| 4,728,194 | 3/1988 | Mori et al. | 356/358 |
| 4,774,615 | 9/1988 | Revelli et al. | 369/110 |
| 4,792,227 | 12/1988 | Yoshizawa | 369/110 |
| 4,841,510 | 6/1989 | Yoshizawa | 369/110 |
| 4,953,124 | 8/1990 | Koyama | 369/110 |
| 5,014,253 | 5/1991 | Morimoto et al. | 369/122 |
| 5,033,828 | 7/1991 | Haruta | 369/110 |
| 5,099,470 | 3/1992 | Matsubayashi | 369/112 |
| 5,153,868 | 10/1992 | Fujinaga | 369/110 |
| 5,221,588 | 6/1993 | Morimoto et al. | 430/19 |

FOREIGN PATENT DOCUMENTS

| | | | |
|---|---|---|---|
| 0292160 | of 1988 | European Pat. Off. | 369/110 |
| 60-143461 | 7/1985 | Japan . | |
| 61-160852 | 7/1986 | Japan . | |
| 63-100648 | of 1988 | Japan | 369/110 |
| 1-223653 | of 1989 | Japan | 369/110 |

OTHER PUBLICATIONS

Birefringence Evaluation System for Magneto-Optical Disc, by Matsui et al., pp. 1–7.
Analysis of Signal to Noise Ratio in Magneto Optical Disk Using a Polarization Simulator, by Toda et al., pp. 273, 274, 277, 280, Denshi Joho Tsushin Gakkai Ronbunshi '88/2 vol. J71-C No. 2.

*Primary Examiner*—Georgia Y. Epps
*Assistant Examiner*—Nabil Hindi
*Attorney, Agent, or Firm*—Parkhurst, Wendel & Rossi

[57] ABSTRACT

In order to measure a phase difference of an opto-magnetic disk having a substrate and a magnetic record layer, linearly polarized light is made incident upon the magnetic layer of the disk from the side of the substrate and light reflected by the disk is received to derive an information signal recorded in the disk, while the opto-magnetic disk is rotated at a usual reproducing speed. A phase compensator arranged in an optical path of the light reflected by the disk is adjusted to change a phase difference introduced by the phase compensator into the light reflected by the disk, while a level of amplitude and/or C/N of the reproduced information signal is monitored. A value of the phase difference introduced by the phase compensator when the amplitude and/or C/N of the reproduced information signal becomes maximum is derived as a measured phase difference of the opto-magnetic disk.

7 Claims, 9 Drawing Sheets

METHOD OF MEASURING PHASE DIFFERENCE OF OPTO-MAGNETIC RECORD MEDIUM AND APPARATUS FOR CARRYING OUT SAID METHOD

This is a continuation of application Ser. No. 07/514,683 filed Apr. 19, 1990, now abandoned.

BACKGROUND OF THE INVENTION

Field of the Invention and Related Art Statement

The present invention relates to method and apparatus for measuring a phase difference of a reflection type opto-magnetic record medium including a substrate and a magnetic record layer applied on the substrate, and more particularly to a method and apparatus for measuring a phase difference due to the birefringence of the substrate and a phase difference due to the Kerr elliptic conversion of the magnetic record layer of the opto-magnetic disk.

In an apparatus for reproducing an information signal recorded in a reflection type an opto-magnetic record medium such as opto-magnetic record disk, linearly polarized light is made incident upon the opto-magnetic disk and the information signal is read out or reproduced by detecting the rotation of the polarization plane of the linearly polarized light reflected from the opto-magnetic disk due to the Kerr effect. An amplitude of the reproduced signal is proportional to $\sin 2\theta_k'$, where $\theta_k'$ is the Kerr rotation angle. Usually the opto-magnetic record disk comprises a substrate made of dielectric material and a record layer made of magnetic material applied on the substrate. In the reproducing apparatus using the opto-magnetic disk, the linearly polarized light is made incident upon the magnetic record layer of the disk through a face of the substrate, so that the light reflected by the magnetic record layer of the opto-magnetic disk is transmitted through the substrate twice. Therefore, the linearly polarized light is converted into elliptically polarized light due to the birefringence of the dielectric substrate which is generally made of synthetic resin such as PMMA (polymethyl methacrylate) or PC (polycarbonate). Further the magnetic layer of the opto-magnetic record disk has such a property that the linearly polarized light is converted into elliptically polarized light. Hereinafter, this is called the Kerr elliptic conversion. That is to say, when the linearly polarized light is made incident upon the magnetic record layer and is reflected thereby, the linearly polarized light is converted into elliptically polarized light and this Kerr elliptic conversion also introduces the phase difference. Due to these phase differences of the opto-magnetic disk, the effective Kerr rotation angle is reduced and thus the amplitude and C/N of the reproduced signal are decreased to a large extent. In the present specification, a sum of the above explained phase differences is sometimes called the total phase difference of the opto-magnetic record medium.

Figure 1:
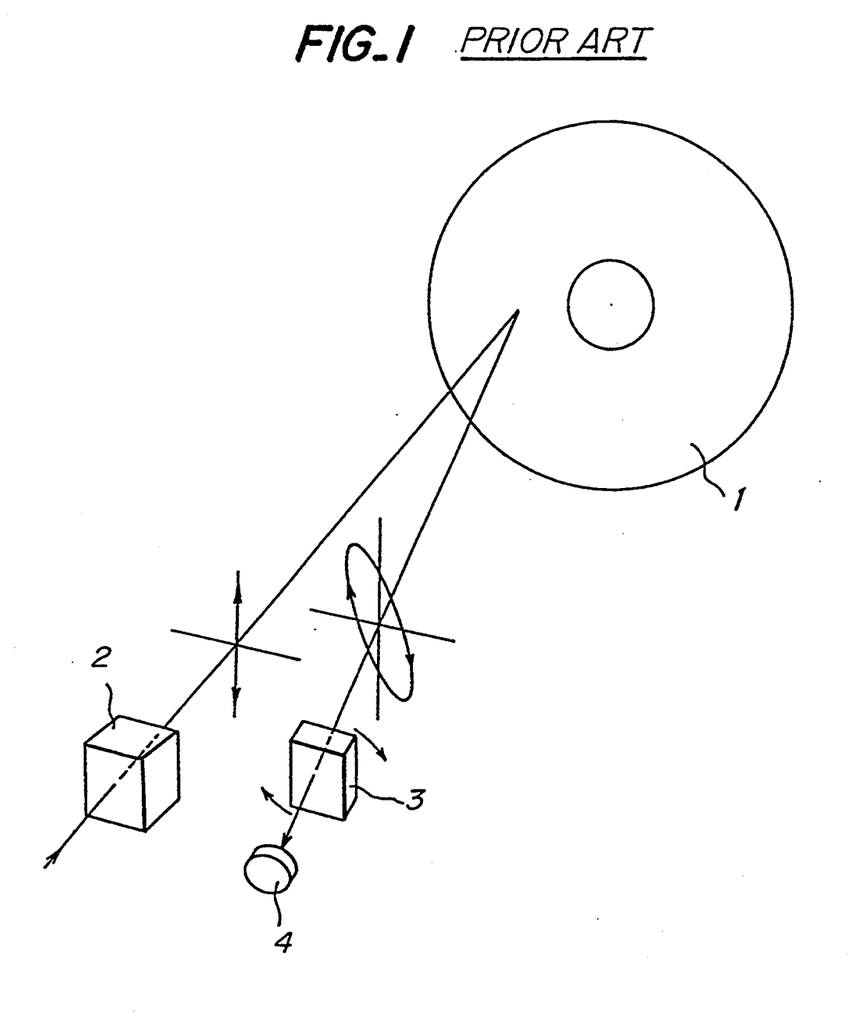
FIG. 1 is a schematic view showing a construction of a known apparatus for measuring the phase difference of the opto-magnetic record disk.

In order to obtain the reproduced signal having a sufficiently large amplitude and C/N, it would be necessary to measure the total phase difference of the opto-magnetic record medium and to manage the manufacturing of the disk. There have been proposed various methods of measuring the phase difference of the opto-magnetic record medium. FIG. 1 is a schematic perspective view showing a known apparatus for measuring the phase difference of the opto-magnetic disk. An opto-magnetic disk 1 is held stationary and a parallel light beam of linearly polarized light is made incident upon the substrate 1 via a polarizer 2 and light reflected by the disk 1 is made incident upon a light receiving element 4 by means of an analyzer 3 which is arranged rotatably. By rotating the analyzer 3 it is possible to measure the phase difference of the opto-magnetic disk 1, i.e. the phase difference between P-polarized light and S-polarized light. However, in this known apparatus, since the parallel light beam is made incident upon the opto-magnetic disk 1, it is impossible to measure the phase difference of the disc accurately, because the birefringence of the substrate varies in accordance with the incident angle of the light. Further, in the known apparatus the measurement is carried out while the opto-magnetic disk 1 is held stationary, so that the actual influence of the phase difference of the disk upon the reproduced signal can not be determined and moreover the measurement can not be effected for the whole surface of the disk 1.

There has been further proposed a known method in which linearly polarized light is made incident upon a substrate and light transmitted through or reflected by the substrate is detected via a phase compensator. However, the known method can not measure the total phase difference of the opto-magnetic disk. That is to say, in the known method, linearly polarized light is made incident upon the substrate and the phase difference due to the birefringence of the substrate is measured. In practice, knowing only the phase difference due to the birefringence of the substrate can not ensure accurate manufacture of the disks. Particularly, in the known phase difference measuring apparatus it is impossible to detect the influence of the phase difference upon the information signal read out of the disks. Therefore, even if the disk is manufactured such that the phase difference of the disk due to the birefringence of the substrate becomes small or zero, it is impossible to obtain the information signal having large signal level and C/N. Further, also in this known phase difference measuring method, the measurement is carried out, while the substrate is held stationary, so that the measurement can not be performed over the whole surface of the substrate. In this manner in the known phase difference measuring method, only the phase difference of the substrate due to the birefringence thereof can be measured locally, so that the disk can not be evaluated correctly.

SUMMARY OF THE INVENTION

The present invention has for its object to provide a method of measuring the total phase difference of the opto-magnetic record medium comprising a substrate and a magnetic record layer applied thereon.

It is another object of the invention to provide a method of measuring the influence of the total phase difference of the opto-magnetic record medium upon a reproduced information signal to derive useful data for managing the construction and manufacture of the opto-magnetic record medium accurately.

It is still another object of the invention to provide a method of measuring a phase difference of the substrate and a phase difference of a magnetic record layer separately from each other, so that it is possible to obtain more precise and useful evaluation data for the construction and manufacture of the opto-magnetic record medium.

According to the invention a method of measuring a phase difference of an opto-magnetic record medium having a substrate and a magnetic record layer applied thereon and having an information signal recorded therein comprises the steps of:

projecting linearly polarized light as a light spot onto the magnetic record layer of the opto-magnetic record medium from the through a side of the substrate;

driving the opto-magnetic record medium with respect to the light spot at a given speed;

receiving light reflected by the opto-magnetic record medium to generate a reproduced information signal;

adjusting a phase difference introduced into the light reflected by the opto-magnetic record medium; and deriving a phase difference of the opto-magnetic record medium from a value of said phase difference introduced into the light reflected by the opto-magnetic record medium when an amplitude and/or C/N of the reproduced information signal becomes maximum.

The present invention also relates to an apparatus for measuring a phase difference of an opto-magnetic record medium and has for its object to provide a novel and useful apparatus for measuring the total phase difference of the opto-magnetic record medium in an accurate manner.

According to the invention, an apparatus for measuring a phase difference of an opto-magnetic record medium including a substrate and a magnetic record medium applied thereon and having an information signal recorded therein comprises, a light source means for emitting linearly polarized light;

a first optical means for projecting the linearly polarized light emitted form the light source means onto the magnetic record layer of the opto-magnetic record medium as a focused light spot through a side of the substrate;

a driving means for moving the opto-magnetic record medium at a given speed with respect to the light spot projected onto the opto-magnetic record medium;

a second optical means for receiving light reflected by the opto-magnetic record medium to reproduce an information signal recorded in the record medium;

a phase compensating means included in the second optical means for changing a phase difference introduced into the light reflected by the opto-magnetic record medium;

a phase indicating means for indicating the phase difference introduced by the phase compensating means into the light reflected by the opto-magnetic record medium; and a signal indicating means for indicating a level and/or C/N of the reproduced information signal; whereby the phase difference of the opto-magnetic record medium is derived from a value of the phase difference introduced by the phase compensating means into the light reflected by the opto-magnetic record medium and a level of amplitude and/or C/N of the reproduced information signal indicated by the signal indicating means.

In a preferable embodiment of the invention, the first optical means comprises a means for rotating the polarizing plane of the light impinging upon the opto-magnetic record medium by 90°, so that a phase difference due to the birefringence of a dielectric substrate of the opto-magnetic record medium and a phase difference due to the Kerr elliptic conversion can be measured separately from each other.

According to the invention the phase compensating means such as Babinet Soleil compensator is arranged in the optical path of the light reflected by an opto-magnetic disk, the light emanating from the compensator is made incident upon a polarizing beam splitter, light fluxes separated by the polarizing beam splitter are received by photodetectors, and outputs of the photodetectors are supplied to a differential amplifier to derive the reproduced information signal. The Babinet Soleil compensator is adjusted such that the amplitude and C/N of the reproduced information signal is a maximum. Then, the total phase difference of the opto-magnetic disk can be calculated from the value of the phase difference introduced by the Babinet Soleil compensator.

It should be noted that the first and second optical means, including an objective lens for projecting the focused beam onto the opto-magnetic record medium and a beam splitter for separating the light reflected by the record medium into S-polarized light and P-polarized light have a phase difference. Thus, even if the opto-magnetic record medium does not have a phase difference, the linearly polarized light reflected from the record medium is converted into elliptically polarized light via the first and second optical means. Then, the effective Kerr rotation angle is reduced and the amplitude of the reproduced signal is also decreased as, illustrated in FIG. 2.

Figure 2:
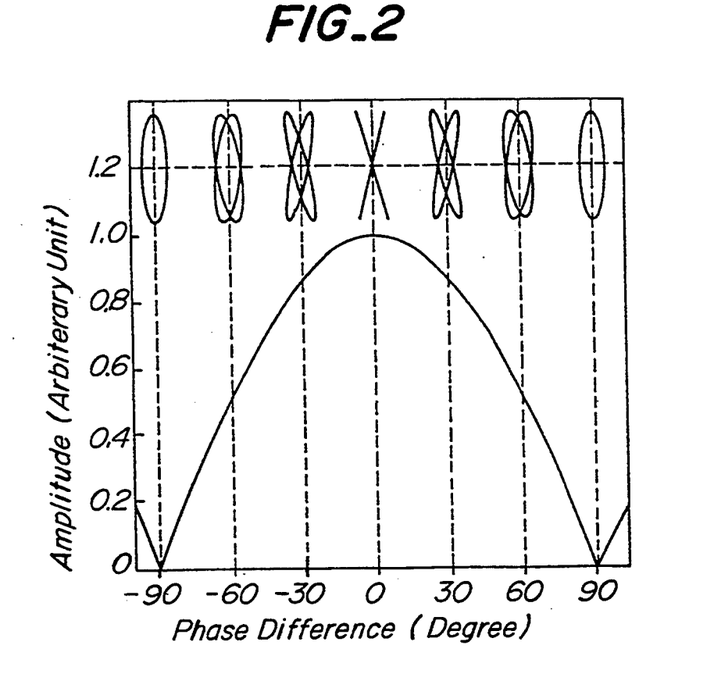
FIGS. 2 and 3 are graphs explaining the principle of the phase difference measuring method according to the invention.

In FIG. 2, the horizontal axis represents the phase difference of the optical system and the vertical axis denotes the amplitude of the reproduced information signal in an arbitrary unit.

In the phase difference measuring apparatus according to the invention, the phase difference of the optical system can be compensated for by the phase compensating means, so that the phase difference of the record medium can be exclusively measured without being affected by the phase difference of the optical system.

Figure 3:
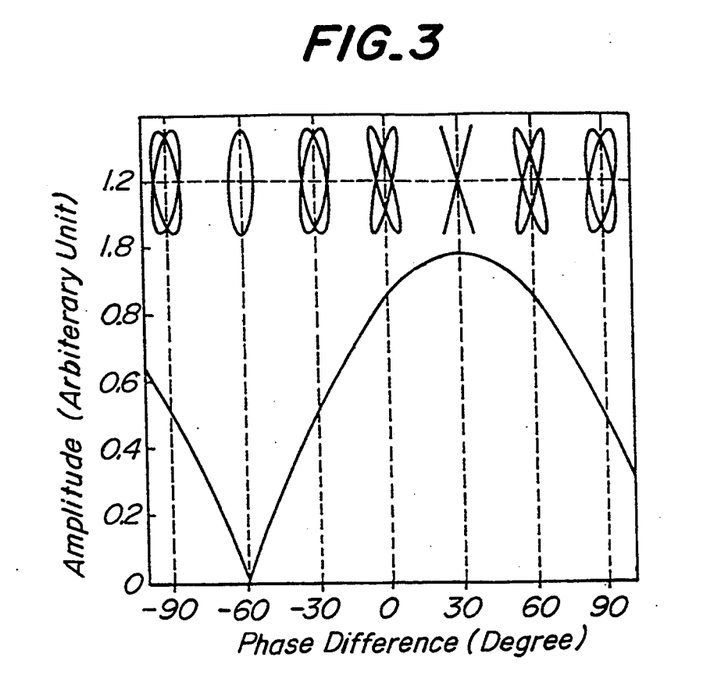

According to the invention, a zero point or an origin of the phase difference introduced by the phase compensating means is set to a value at which the phase difference of the optical system except for the phase compensating means is just compensated for. This zero point value of the phase difference introduced by the phase compensator may be determined in various ways. For instance, phase differences of all optical elements constituting the optical system are separately measured and a sum of the thus measured phase differences is set as the zero point value. Then, the information signal recorded in the opto-magnetic disk is reproduced while the phase difference introduced by the phase compensating means is continuously changed. During this measurement, the amplitude of the reproduced signal changes as shown by a curve in FIG. 3. That is to say, the amplitude of the reproduced signal becomes maximum at a phase difference of 30 degrees. Then it can be recognized that the relevant opto-magnetic disk has the total phase difference of 30 degrees. As stated above, since the phase compensating means is adjusted to compensate the phase difference of the optical system, it is possible to measure the phase difference of the opto-magnetic disk in an accurate manner without being affected by the phase difference of the optical system.

Now the principal of the phase difference measuring technique according to the present invention will be explained in more detail. When linearly polarized light is made incident upon the opto-magnetic record disk, the polarization plane of light reflected by the disk is rotated by an angle $\theta_K'$ due to the Kerr effect and after that the light is subjected to a phase difference $\delta$ between the p-polarized light whose electric vector oscillating plane is the same as that of the incident plane and the S-polarized light whose electric vector oscillating plane is perpendicular to the polarizing direction of the incident plane. For the sake of simplicity, it is assumed that the principal axis of the birefringence of the substrate of the disk is coincident with the polarizing direction of the incident linearly polarized light. When the phase difference due to the birefringence of the substrate of the disk is represented as $\Delta$ and the phase difference of the optical system is termed as $\phi$, the polarizing condition of the light which is made incident upon the photodetectors can be represented by the following Jones vector:

$$\begin{bmatrix} E_x^\pm \\ E_y^\pm \end{bmatrix} = \begin{bmatrix} \exp i(\phi + \Delta + \delta)/2 & 0 \\ 0 & \exp[-i(\phi + \Delta + \delta)/2] \end{bmatrix} \cdot \quad (1)$$

$$\begin{bmatrix} \cos(\pm \theta_K') & \sin(\pm \theta_K') \\ -\sin(\pm \theta_K') & \cos(\pm \theta_K') \end{bmatrix} \cdot \begin{bmatrix} 0 \\ 1 \end{bmatrix} =$$

$$\begin{bmatrix} \exp i(\phi + \Delta + \delta)/2 & \cdot & \sin(\pm \theta_K') \\ -\sin[-i(\phi + \Delta + \delta)/2] & \cdot & \cos(\pm \theta_K') \end{bmatrix}$$

Then, an amplitude A of the reproduced signal which is derived by the differential manner with the aid of the analyzer having the optical axis of 45° can be written by the following equation.

$$\begin{aligned} A &= e_x^+ \cdot e_x^{+*} \cdot e_x^- \cdot e_x^{-*} \\ &= \sin 2\theta_K' \cos(\phi + \Delta + \delta) \end{aligned} \quad (2)$$

wherein $$\begin{bmatrix} e_x^\pm \\ e_y^\pm \end{bmatrix} = 1/\sqrt{2} \cdot \begin{bmatrix} 1 & 1 \\ -1 & 1 \end{bmatrix} \cdot \begin{bmatrix} E_x^\pm \\ E_y^\pm \end{bmatrix} \quad (3)$$

Therefore, it can be understood that the amplitude A of the reproduced signal is changed in accordance with a cosine curve of the phase difference introduced by the phase compensating means. Further it can be understood that the maximum amplitude of the reproduced information signal is obtained when the condition of $\phi = -(\Delta + \delta)$ is satisfied, i.e., when the total phase difference of the opto-magnetic disk and the phase difference of the optical system including the phase difference introduced by the phase compensating means have the same value, but have the opposite signs. Therefore, when the disk is driven and the reproduced information signal is monitored, it is possible to measure the total phase of the disk by detecting the phase difference introduced by the phase compensating means when the level and/or C/N of the reproduced signal become maximum. According to the invention, the phase difference of the opto-magnetic disk is measured by detecting the information signal record in the opto-magnetic disk, so that the phase difference of the disk under the normal reproducing condition can be measured and thus the opto-magnetic disk can be evaluated much more accurately and the construction and manufacture of the disk can be managed precisely. That is to say, the phase difference measured by the apparatus according to the invention can be utilized to design or determine constructions and materials of the substrate and magnetic layer of the opto-magnetic record medium and to control a process of injection molding of the substrate.

In the above mentioned equations, the phase difference $\Delta$ due to the birefringence of the substrate is assumed to be the phase difference between the phase of the light whose polarizing direction is parallel with that of the incident linearly polarized light and the light whose polarizing direction is perpendicular to that of the incident polarized light. From this it can be derived that when the polarizing plane of the incident linearly polarized light is rotated by 90 degrees, the positional relation of the polarization planes with respect to the phase advancing and delaying axes are inverted, so that the sign or polarity of the phase difference $\Delta$ is inverted.

Now it is assumed that phase differences of the optical system which give the maximum amplitude of the reproduced information signal are denoted by $\phi\|$ and $\phi\bot$, respectively when the polarizing direction of the incident linearly polarized light is made parallel with and perpendicular to a groove formed in the opto-magnetic record medium. Then, the following equations can be obtained.

$$\left. \begin{aligned} \phi\| &= -(\Delta + \delta) \\ \phi\bot &= -(-\Delta + \delta) \end{aligned} \right\} \quad (4)$$

Therefore, the phase difference 6 of the opto-magnetic record medium due to the Kerr elliptic conversion and the phase difference A of the opto-magnetic record medium due to the birefringence of the substrate can be measured separately from each other in the following manner.

$$\left. \begin{aligned} \delta &= -(\phi\| + \phi\bot)/2 \\ \Delta &= -(\phi\| - \phi\bot)/2 \end{aligned} \right\} \quad (5)$$

In the manner explained above, according to the invention it is possible to measure the phase difference due to the substrate and magnetic record layer separately from each other, and thus very useful data for managing the construction and manufacturing of the opto-magnetic record medium can be obtained accurately.

DESCRIPTION OF THE PREFERRED EMBODIMENTS

Figure 4A:
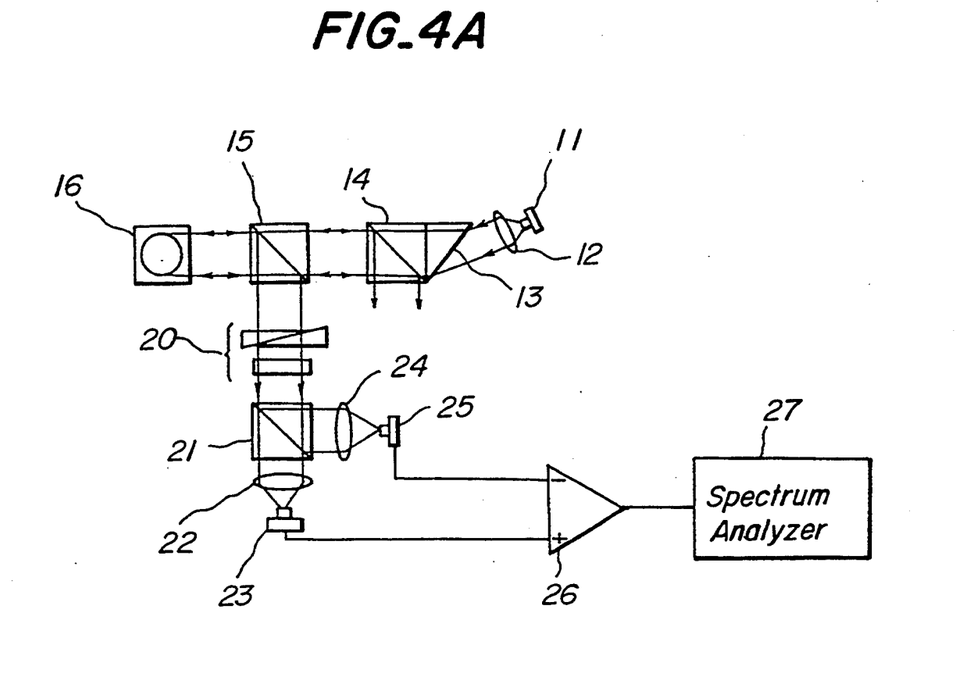
FIGS. 4A and 4B are plan and side views, respectively illustrating an embodiment of the phase difference measuring apparatus according to the invention.
Figure 4B:
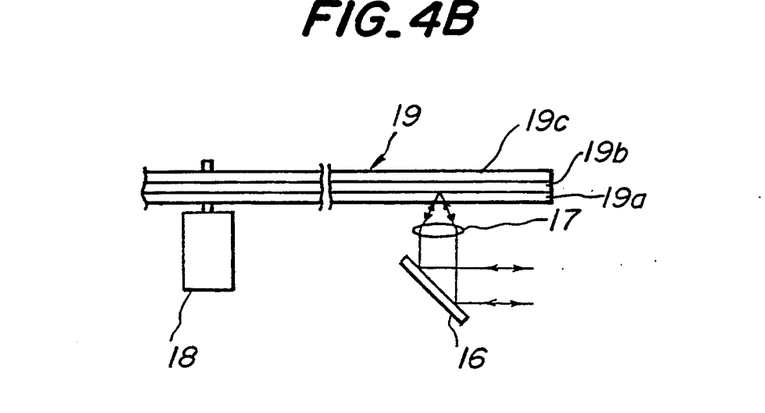

FIGS. 4A and 4B show an embodiment of the apparatus according to the invention for measuring the phase difference of an opto-magnetic disk. Laser light emitted by a semiconductor laser 11 is made incident upon a polarizing beam splitter 15 by means of collimator lens 12, beam shaping prism 13 and half mirror 14. Linearly polarized light transmitted through the beam splitter 15 is made incident upon an opto-magnetic disk 19 via reflection mirror 16 and objective lens 17 as illustrated in FIG. 4B. The disk 19 is rotated by a spindle motor 18 at a given revolving speed. The disk 19 has one or more information tracks recorded therein and comprises substrate 19a, magnetic record layer and protection film. The light beam is made incident upon the disk 19 such that the polarizing direction of the incident light is tangential to the direction of the information track or perpendicular to the information track.

Light reflected by the opto-magnetic disk 19 is made incident upon the polarizing beam splitter 15 by means of the objective lens 17 and reflection mirror 16. Light transmitted through the beam splitter 15 and reflected by the half mirror 14 is introduced to a servo signal detecting system now shown to derive focusing and tracking error signals. By means of the focusing and tracking error signals the objective lens 17 is driven such that the light spot is always made incident upon the information track formed in the disk 19 as a correctly focused spot. Since the focusing and tracking servo mechanisms are well known in the art, its explanation is dispensed with.

A part of the light reflected by the disk 19 is reflected by the beam splitter 15 and is then made incident upon another polarizing beam splitter 21 via a phase compensator formed by Babinet Soleil phase compensator 20. The light transmitted through the beam splitter 21 is received by a photodetector 23 by means of a lens 22 and the light reflected by the beam splitter is collected by a lens 24 and is received by a photodetector 25. Output signals from the photodetectors 23 and 25 are supplied to a differential amplifier 26 to derive a difference therebetween which represents a reproduced information signal recorded in the disk 19. The reproduced signal thus obtained is supplied to a spectrum analyzer 27.

Figure 5A:
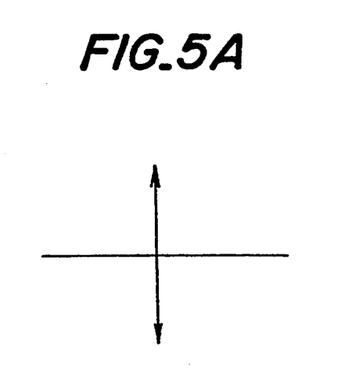
FIGS. 5A, 5B and 5C and FIGS. 6A and 6B are diagrams showing the operation of the apparatus shown in FIGS. 4A and 4B.
Figure 5B:
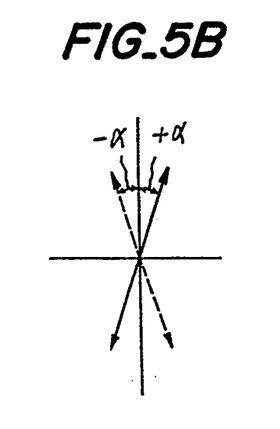
Figure 6A:
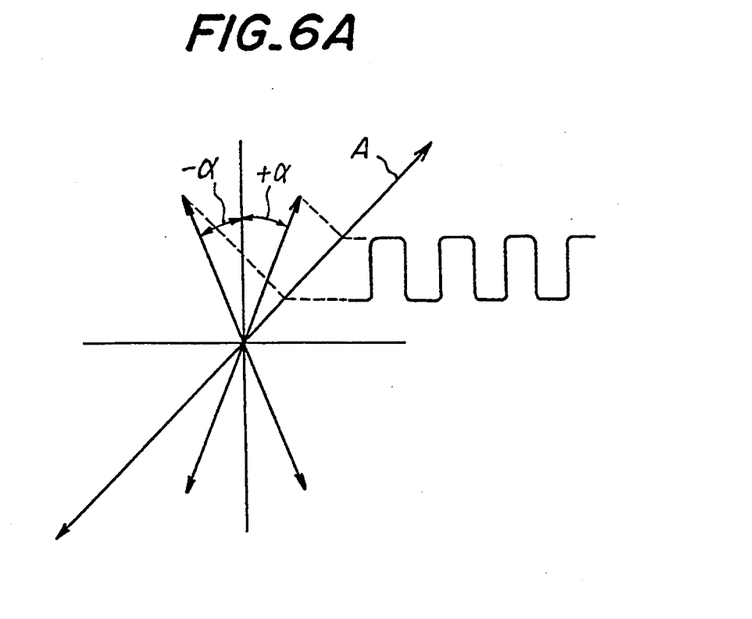

Now the method of measuring the phase difference of the opto-magnetic disk 19 will be explained. At first the phase difference of the optical system excluding the phase compensator 20 is measured. This can be effected by measuring phase differences of all optical elements in the system and then calculating a sum of the thus measured phase differences. Alternatively the phase difference of the optical system may be measured by using a standard opto-magnetic disc having a known phase difference. Then, the origin or zero point of the phase compensator 20 is set to such a value which is equal to the phase difference of the optical system, but has an opposite sign. When the phase difference measuring apparatus is formed as an automatic one having CPU, said phase difference of the optical system has to be entered into the CPU. In the present embodiment, the apparatus is constructed as a manual one, the measured phase difference of the optical system has to be memorized manually. Then an opto-magnetic disk 19 whose phase difference has to be measured is set and is rotated by the spindle motor 18 at a speed at which usual disks are rotated to reproduce the information signals therefrom. Then, linearly polarized light shown by a double headed arrow in FIG. 5A is made incident upon the disk 19. If it is assumed that the disk has no phase difference, then the polarizing direction of the light reflected by the disk is rotated as illustrated in FIG. 5B in a direction which is dependent upon the direction of the magnetization in the magnetic record layer 19b due to the Kerr effect. That is to say, the polarizing direction of the linearly polarized light is rotated by angles $\pm \alpha$. Therefore, by arranging the polarizing beam splitter 21 such that its orientating angle makes an angle of 45 degrees with respect to the polarizing direction of the incident linearly polarized light as depicted by an arrow A in FIG. 6A, it is possible to obtain the reproduced information signal having a high C/N from the differential amplifier 26.

Figure 5C:
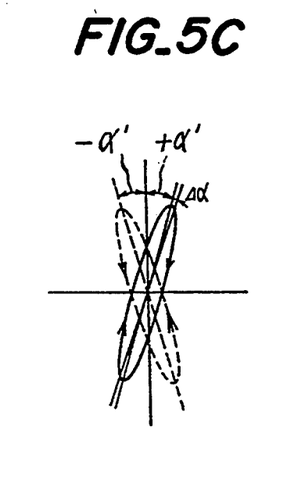
Figure 6B:
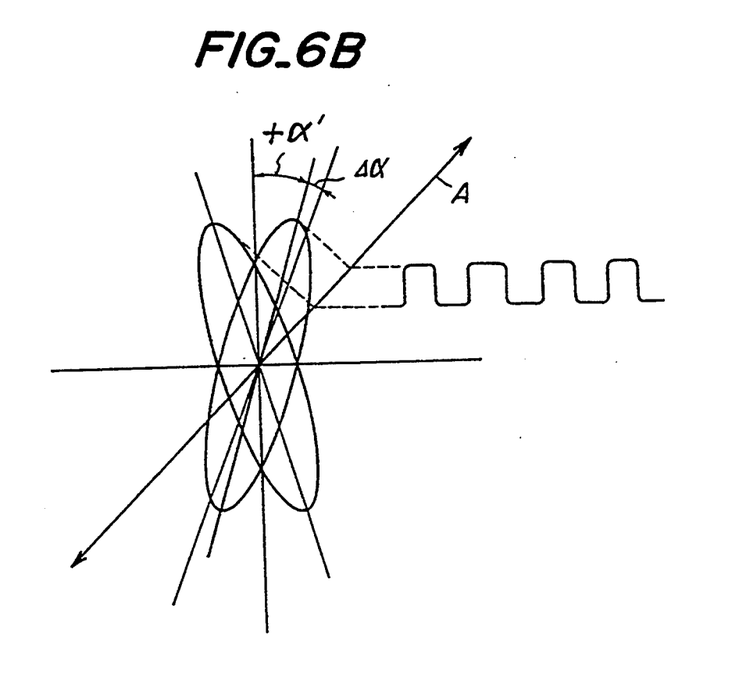

In practice, the opto-magnetic disk 19 has the phase difference due to the birefringence of the substrate 19a and the Kerr elliptic conversion of the magnetic record layer 19b, and therefore the light reflected by the disk is converted into elliptically polarized light as shown in FIG. 5C. Then the Kerr rotation angles $\pm \alpha$ are changed into smaller angles $\pm \alpha'$ between the major axes of ellipses and the polarizing direction of the incident linearly polarized light. That is to say, the rotation angle is reduced by $\Delta \alpha$ than $\alpha$. Therefore, the amplitude of the reproduced signal supplied from the differential amplifier 26 becomes smaller as illustrated in FIG. 6B. Therefore, it is desired that the opto-magnetic disk should have the phase difference as small as possible, and to this end the phase difference of the disk has to be measured precisely.

In the present embodiment, while the opto-magnetic disk 19 is rotated at the usual reproducing speed, the phase difference introduced by the phase compensator 20 in the reflected light is changed over a predetermined range. During this, the amplitude of the reproduced information signal is detected. In the present embodiment, a component having a frequency of 3.7 MHz is selected by the spectrum analyzer 27 and the amplitude and C/N of the thus selected frequency component are detected. The frequency of 3.7 MHz is the highest signal component of the reproduced information signal. It should be noted that the higher the frequency is, the larger the influence of the phase difference of the disk becomes. From the data thus detected, the phase difference introduced by the phase compensator 20 which gives the maximum amplitude and/or C/N is detected. Then the thus detected phase difference denotes the phase difference of the opto-magnetic disk 19. In order to detect an amount of the phase difference introduced by the phase compensator 20 there is provided a means for indicating an amount of the adjustment of the phase compensator 20. It should be noted that according to the present invention the phase difference of the disk can be measured in a fully automatic manner or a semi-automatic manner or a manual manner. In the fully automatic measurement, the phase compensator is automatically driven to change the phase difference introduced into the light reflected by the disk in accordance with a predetermined manner with the aid of a program stored in CPU, and at the same time the output signal supplied from the spectrum analyzer 27 is stored in CPU. Then CPU can calculate the phase difference which gives the maximum amplitude and/or C/N of the reproduced information signal. In the manual measurement, the phase difference introduced by the phase comparator and the amplitude and/or C/N of the reproduced signal supplied from the spectrum analyzer 27 are manually recorded and then the phase difference which shows the maximum amplitude and/or C/N is found manually.

Figure 7:
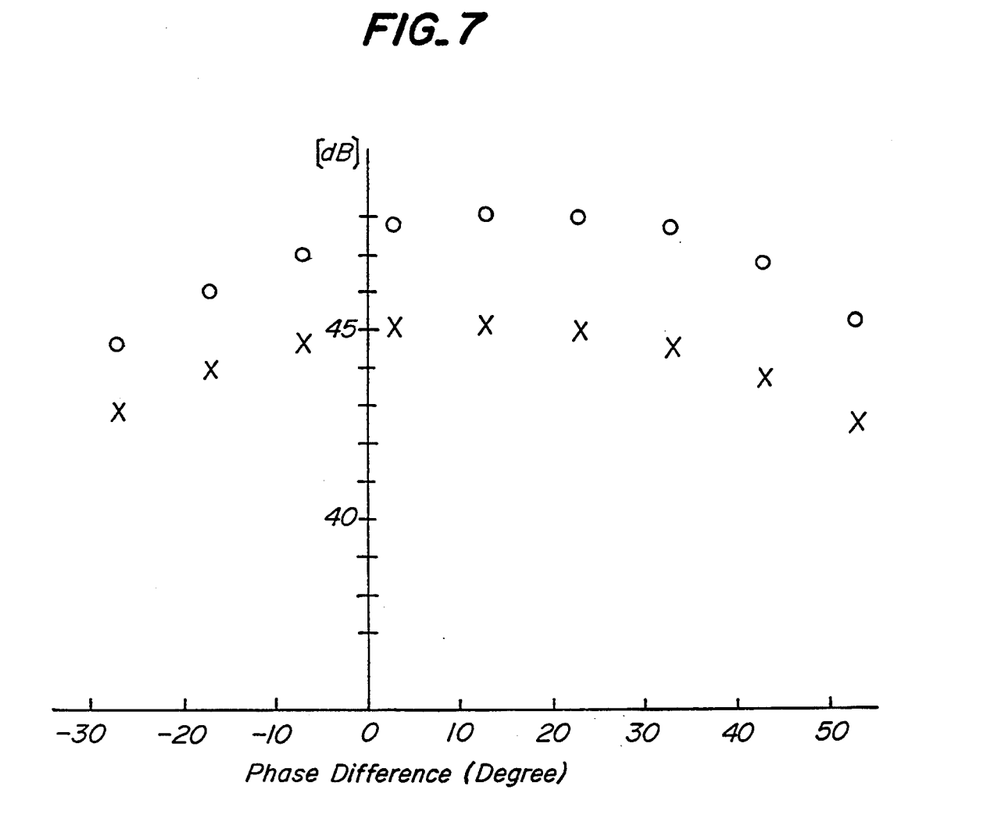
FIGS. 7 and 8 are graphs representing experimental results obtained by the apparatus of FIGS. 4A and 4B.
Figure 8:
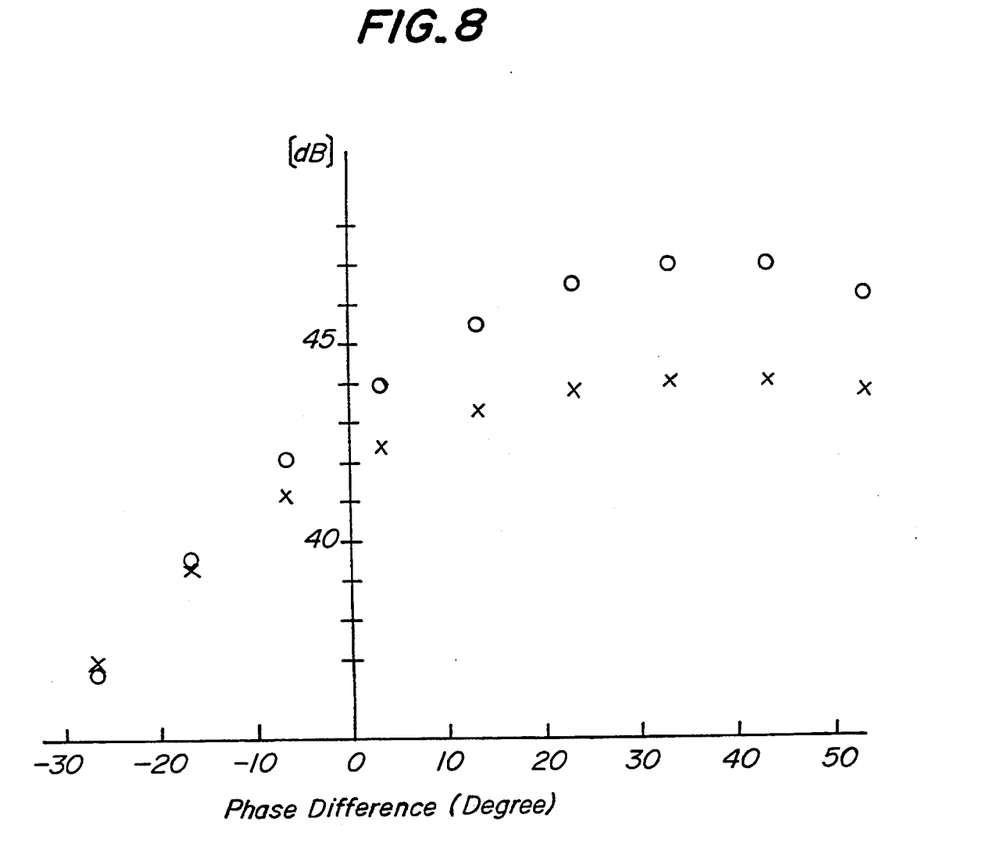

FIGS. 7 and 8 show actual measurement results of two kinds of disks. In these graphs, the horizontal axis denotes the phase angle introduced by the phase compensator 20 and the vertical axis represents the amplitude and C/N of the reproduced information signal having the frequency of 3.7 MHz. The amplitude is expressed by cross marks X and the C/N (carrier to noise ratio) is shown by circles ◯. In the disk shown in FIG. 7, at zero phase difference the amplitude and C/N of the reproduced information signal have levels higher than 45 dBs, and these levels become maximum when the phase difference of about 13 degrees is introduced by the phase compensator 20. Then it is judged that the opto-magnetic disk has the total phase difference of about 13 degrees. In usual apparatuses for reproducing the information signals from the opto-magnetic disks, when the amplitude and C/N of the reproduced signal have levels larger than 45 dBs, the disk is sufficiently usable.

In the opto-magnetic disk illustrated in FIG. 8, levels of the amplitude and C/N of the reproduced information signal are smaller than 45 dBs, and these levels become maximum when the phase difference of about 35 degrees is introduced into the reflected light. Then it can be judged that the relevant disk has the total phase difference of about 35 degrees and thus is not suitable for the practical use.

Figure 9:
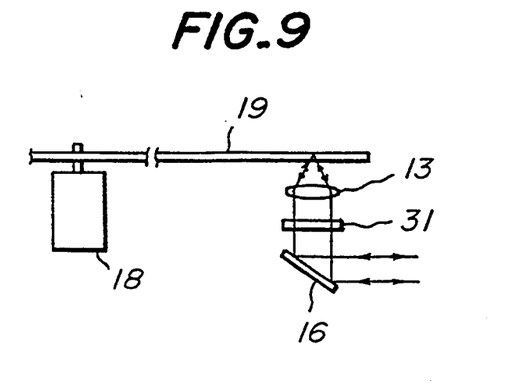
FIG. 9 is a side view depicting a major portion of another embodiment of the apparatus according to the invention.

FIG. 9 is a schematic view showing a major portion of another embodiment of the phase difference measuring apparatus according to the present invention. In the present embodiment, between the reflection mirror 16 and the objective lens 17 is arranged a half wavelength plate 31. The half wavelength plate 31 is provided rotatably over 45 degrees, so that the direction of the polarizing plane of the incident linearly polarized light can be rotated over 90 degrees. That is to say, by rotating the half wavelength plate 31, the polarizing direction of the incident linearly polarized light can be aligned to be parallel with grooves in the disk and perpendicular to the grooves. In this manner in the present embodiment it is possible to measure the phase differences $\phi \parallel$ and $\phi \perp$. The remaining construction of the present embodiment is same as that of the previous embodiment.

Figure 10:
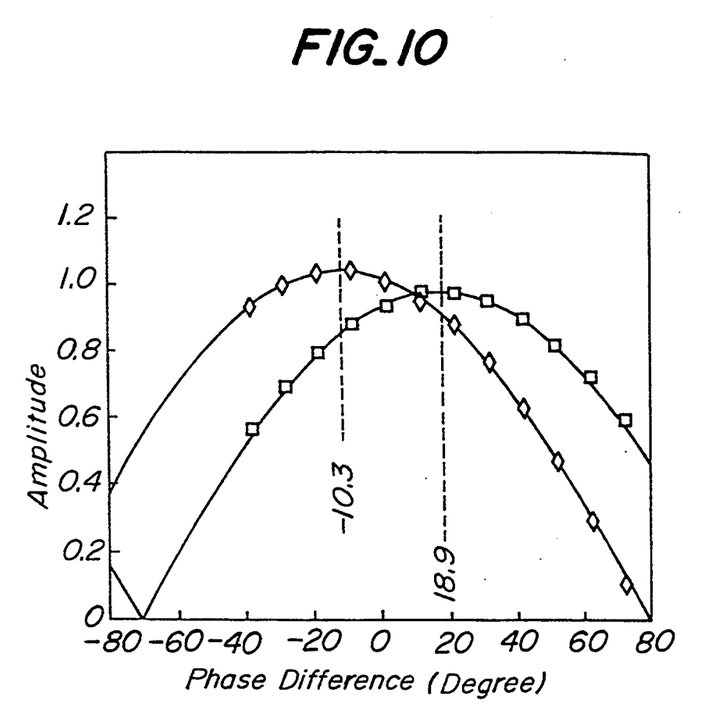
FIGS. 10, 11 and 12 are graphs showing experimental results obtained by the apparatus shown in FIG. 9.
Figure 11:
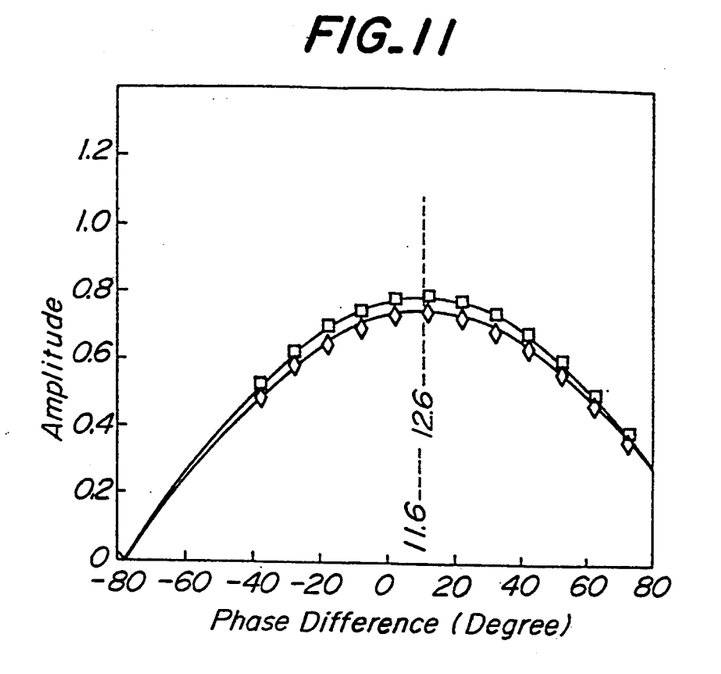
Figure 12:
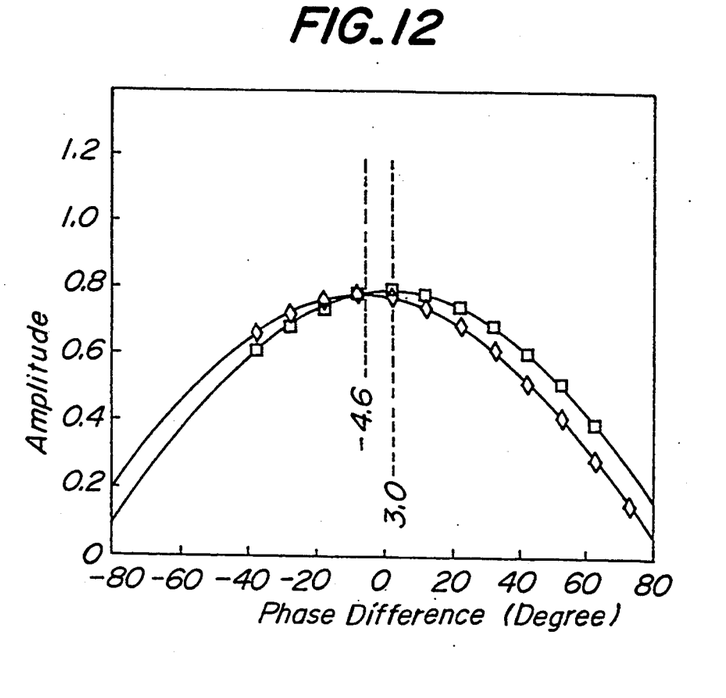

FIGS. 10, 11 and 12 are graphs showing results of experiments carried out by the apparatus shown in FIG. 9. In these graphs, the horizontal axis denotes the phase difference introduced by the phase compensator and the vertical axis represents an amplitude of the reproduced information signal of 3.7 MHz averaged over one revolution of opto-magnetic disks. Rectangular marks □ show the phase difference $\phi \parallel$ and rhombic marks denote the phase difference $\phi \perp$. It should be noted that measured values have been subjected to cosine fitting.

FIG. 10 shows the measurement result of an opto-magnetic disk which has a substrate made of polycarbonate. In this disk, the phase differences $\phi \parallel$ and $\phi \perp$ giving the maximum amplitude of the reproduced information signal are 18.9 and −10.3 degrees, respectively.

Then the phase difference due to the birefringence of the substrate $\delta$ and the phase difference due to the Kerr elliptic conversion $\Delta$ can be calculated as follows by using the equations (5).

$\delta = -4.3$ degrees $\Delta = -14.6$ degrees

From the results it is find that this disk has the phase angle due to the birefringence of the substrate amounts to about 15 degrees.

FIG. 11 represents the experimental results of an opto-magnetic disk having a substrate made of glass. In this disk the phase differences $\phi \parallel$ and $\phi \perp$ are 11.6 and 12.0 degrees, respectively. Therefore, the phase differences due to the birefringence of the substrate and due to the Kerr elliptic conversion are calculated as follows.

$\delta = -11.8$ degrees $\Delta = 0.2$ degrees

In this disk it is found that the magnetic record layer introduces the phase difference $\delta$ of about 12 degrees.

FIG. 12 shows the results of experiment for an opto-magnetic disk having a substrate made of non-crystalline non-saturated alphatic plastics. In this disk, the phase differences giving the maximum amplitude of the reproduced information signal $\phi \parallel$ and $\phi \perp$ are 3.0 and −4.6 degrees, respectively. Therefore, the phase differences due to the birefringence and due to the Kerr elliptic conversion are calculated as follows.

$\delta = 0.8$ degrees $\Delta = -3.8$ degrees

It should be noted that the above experimental results are similar to the general tendency of the opto-magnetic disks having the substrates made of birefringence materials. Further, by means of the second embodiment just explained above, it is possible to measure the phase difference due to the birefringence of the substrate as well as the phase difference due to the Kerr elliptic conversion separately from each other, and thus the opto-magnetic disk can be evaluated accurately and very useful data for managing the formation of the disk can be obtained.

As explained above in detail, according to the present invention, the phase difference of the opto-magnetic record medium can be measured while the amplitude and/or C/N of the reproduced information signal are monitored, so that it is possible to obtain very useful data for evaluating the record medium correctly and accurately. Further the phase difference due to the birefringence of the substrate and the phase difference due to the Kerr elliptic conversion of the magnetic layer can be measured separately from each other, so that the development of improved record medium and the detailed analysis of prototype record medium can be expected.

The present invention is not limited to the embodiments just explained above, but many alternations and modifications can be conceived by those skilled in the art within the scope of the invention. In the above embodiments the phase compensator is formed by the Babinet Soleil compensator, but it may be constituted by other phase compensating elements such as Ehringhaus compensator. Further in the first embodiment, the phase difference of the opto-magnetic disk is measured by detecting both the amplitude level and C/N of the reproduced information signal, but it is also possible to detect only one of the amplitude and C/N. In the second embodiment, the phase difference is measured by detecting the average level of the amplitude of the reproduced information signal, but it is also possible to detect both the amplitude and C/N of the readout signal or only C/N of the signal.

Moreover, in the second embodiment, the direction of the polarizing plane of the incident linearly polarized light is changed by 90 degrees by rotating the half wavelength plate by 45 degrees, but the same effect can be attained by detachably providing a 90 degrees rotator. Furthermore, although the present invention is preferably applied to the opto-magnetic record disk, the present invention may be equally applied to measure the phase difference of a card-like opto-magnetic record medium.

What is claimed is:

1. A method of measuring a phase difference of an opto-magnetic record medium comprising a substrate, a magnetic record layer applied thereon and an information signal recorded therein, comprising the steps of:

projecting linearly polarized light as a light spot onto the magnetic record layer of the opto-magnetic record medium through said substrate, said linearly polarized light being polarized in a polarizing direction;

driving the opto-magnetic record medium with respect to the light spot at a given speed;

receiving light reflected by the opto-magnetic record medium to generate a reproduced information signal;

adjusting a phase difference introduced into the light reflected by the opto-magnetic record medium;

deriving a total phase difference of the opto-magnetic record medium from a value of said phase difference introduced into the light reflected by the opto-magnetic record medium after adjustment thereof when an amplitude and/or C/N of the reproduced information signal becomes maximum; and changing said polarizing direction of the linearly polarized light by 90 degrees to measure, from said total phase difference, a phase difference due to birefringence of said substrate and a phase difference due to Kerr elliptic conversion from said magnetic record medium separately from each other.

2. The method of claim 1, wherein said step of adjusting said phase difference introduced into the light reflected by the opto-magnetic record medium is effected by adjusting a Babinet Soleil compensator arranged in a light path of said light reflected by the opto-magnetic record medium.

3. The method of claim 1, wherein said step of adjusting said phase difference introduced into the light reflected by the opto-magnetic record medium is effected by adjusting an Ehringhaus compensator arranged in a light path of said light reflected by the opto-magnetic record medium.

4. An apparatus for measuring a phase difference of an opto-magnetic record medium comprising a substrate, a magnetic record medium applied thereon and an information signal recorded therein, comprising:

a light source means for emitting linearly polarized light, said linearly polarized light being polarized in a polarizing direction;

a first optical means for projecting the linearly polarized light emitted from said light source means onto said magnetic record layer of the opto-magnetic record medium as a focused light spot, said linearly polarized light passing through said substrate;

a driving means for moving the opto-magnetic record medium at a given speed with respect to said focused light spot;

a second optical means for receiving light reflected by the opto-magnetic record medium to generate a reproduced information signal recorded in said record medium;

an adjustable phase compensating means included in said second optical means for changing a phase difference introduced into the light reflected by the opto-magnetic record medium;

a phase indicating means for indicating the phase difference introduced by said phase compensating means into the light reflected by said opto-magnetic record medium;

a signal indicating means for indicting at least one of an amplitude and C/N of the reproduced information signal, whereby a total phase difference of the opto-magnetic record medium is derived from the phase difference introduced by said adjustable phase compensating means; and a phase rotating means included in said first optical means for rotating said polarizing direction of the linearly polarized light to measure, from said total phase difference of the opto-magnetic record medium, a phase difference due to birefringence of the substrate and a phase difference due to Kerr elliptic conversion of the magnetic record layer separately from each other.

5. The apparatus of claim 4, wherein said phase rotating means comprises a half wavelength plate rotatable by at least 45 degrees.

6. The apparatus of claim 4, wherein said adjustable phase compensating means comprises a Babinet Soleil compensator.

7. The apparatus of claim 4, wherein said adjustable phase compensating means comprises an Ehringhaus compensator.

* * * * *